(12) United States Patent
Iwase et al.

(10) Patent No.: US 7,936,460 B2
(45) Date of Patent: May 3, 2011

(54) SENSOR UNIT IN EXHAUST GAS ANALYZER

(75) Inventors: Tomoyasu Iwase, Aichi-gun (JP); Katsutoshi Goto, Okazaki (JP); Masahiro Yamakage, Anjo (JP); Tokio Okano, Toyota (JP); Yoshihiro Deguchi, Yokohama (JP); Minoru Danno, Yokohama (JP); Masazumi Tanoura, Yokohama (JP); Masao Watanabe, Kobe (JP); Satoshi Fukada, Kobe (JP)

(73) Assignees: Toyota Jidosha Kabushiki Kaisha, Toyota (JP); Mitsubishi Heavy Industries, Ltd., Tokyo (JP)

( * ) Notice: Subject to any disclaimer, the term of this patent is extended or adjusted under 35 U.S.C. 154(b) by 60 days.

(21) Appl. No.: 12/224,793

(22) PCT Filed: May 29, 2007

(86) PCT No.: PCT/JP2007/061245
§ 371 (c)(1),
(2), (4) Date: Sep. 5, 2008

(87) PCT Pub. No.: WO2007/139223
PCT Pub. Date: Dec. 6, 2007

(65) Prior Publication Data
US 2009/0095918 A1    Apr. 16, 2009

(30) Foreign Application Priority Data
May 31, 2006 (JP) ................. 2006-151536

(51) Int. Cl.
*G01N 21/00* (2006.01)
(52) U.S. Cl. .......... 356/438; 73/23.2; 73/1.06; 356/444; 356/432; 250/339.1; 250/339.05

(58) Field of Classification Search .......... 356/432–444; 250/338.1, 339.01, 339.05–339.08, 341.8; 73/23.2, 1.06, 23.31
See application file for complete search history.

(56) References Cited

U.S. PATENT DOCUMENTS
3,207,026 A    9/1965    Churchill et al.
(Continued)

FOREIGN PATENT DOCUMENTS
DE    199 04 691 A1    9/2000
(Continued)

OTHER PUBLICATIONS

Yamakage et al., "Chokusetsu Kooto Engine Hai-gas Keisoku Gijutsu no Kaihatsu (Sonol)," *Preprints of Meeting on Automotive Engineers*, No. 12-07, May 23, 2007, pp. 21-24.

(Continued)

*Primary Examiner* — Gregory J Toatley
*Assistant Examiner* — Iyabo S Alli
(74) *Attorney, Agent, or Firm* — Oliff & Berridge, PLC

(57) ABSTRACT

An exhaust gas analyzer of the present invention includes a sensor unit 11 installed in an exhaust path from an engine, applies laser light to exhaust gas emitted from the engine and receives laser light that has passed through the exhaust gas so as to measure the concentration of a component contained in the gas based on the received laser light. To an aperture 16 formed in a sensor base 15 of the sensor unit 11, an adjustment ring 40 in a circumferential face of which small holes 41 serving as a laser light passage portion is formed and whose inner circumferential face serves as an exhaust gas passage opening 21 is detachably fitted, whereby the sensor unit can be attached so as to conform to different inner diameters of exhaust tubes.

7 Claims, 8 Drawing Sheets

U.S. PATENT DOCUMENTS

| | | | |
|---|---|---|---|
| 3,958,122 A | | 5/1976 | Jowett et al. |
| 4,432,649 A | | 2/1984 | Krause |
| 5,060,505 A | | 10/1991 | Tury et al. |
| 5,096,834 A | | 3/1992 | Saito |
| 5,173,749 A | * | 12/1992 | Tell et al. ............... 356/437 |
| 5,275,553 A | | 1/1994 | Frish et al. |
| 5,572,031 A | | 11/1996 | Cooper et al. |
| 6,107,631 A | | 8/2000 | He |
| 6,150,661 A | | 11/2000 | McCaul et al. |
| 6,154,284 A | | 11/2000 | McAndrew et al. |
| 6,496,258 B1 | | 12/2002 | Leipertz et al. |
| 6,542,831 B1 | | 4/2003 | Moosmuller et al. |
| 6,674,528 B2 | | 1/2004 | Adachi et al. |
| 6,809,825 B2 | | 10/2004 | Kaufmann |
| 7,041,153 B2 | | 5/2006 | Totoki |
| 7,365,352 B2 | | 4/2008 | Muta et al. |
| 7,650,780 B2 | | 1/2010 | Hall |
| 2003/0160174 A1 | | 8/2003 | Grant et al. |
| 2004/0064243 A1 | | 4/2004 | Nakamura |
| 2004/0237505 A1 | * | 12/2004 | Leipertz ............... 73/23.32 |
| 2006/0256330 A1 | | 11/2006 | Leipertz |
| 2009/0039284 A1 | * | 2/2009 | Goto et al. ............ 250/432 R |

FOREIGN PATENT DOCUMENTS

| | | |
|---|---|---|
| DE | 101 50 970 A1 | 4/2003 |
| DE | 103 09 604 A1 | 9/2004 |
| EP | 0 768 521 A1 | 4/1997 |
| EP | 1 398 617 A1 | 3/2004 |
| JP | A-55-83839 | 6/1980 |
| JP | U 63-107845 | 7/1988 |
| JP | B2-64-1740 | 1/1989 |
| JP | A-3-25352 | 2/1991 |
| JP | A-3-31726 | 2/1991 |
| JP | A-3-107744 | 5/1991 |
| JP | A-3-505131 | 11/1991 |
| JP | A-4-16749 | 1/1992 |
| JP | A 4-27846 | 1/1992 |
| JP | A-6-148072 | 5/1994 |
| JP | A-8-54339 | 2/1996 |
| JP | A 8-278179 | 10/1996 |
| JP | A-8-338805 | 12/1996 |
| JP | B2-5-77023 | 10/1998 |
| JP | B2-2837442 | 10/1998 |
| JP | A-11-83734 | 3/1999 |
| JP | A-11-325427 | 11/1999 |
| JP | A-2000-74830 | 3/2000 |
| JP | A-2000-206041 | 7/2000 |
| JP | A-2000-510950 | 8/2000 |
| JP | A-2000-283915 | 10/2000 |
| JP | A-2000-314345 | 11/2000 |
| JP | A-2001-74653 | 3/2001 |
| JP | A-2001-124674 | 5/2001 |
| JP | A-2001-174410 | 6/2001 |
| JP | A-2002-48711 | 2/2002 |
| JP | A-2002-506222 | 2/2002 |
| JP | A-2002-131198 | 5/2002 |
| JP | A 2003-114192 | 4/2003 |
| JP | A 2003-139701 | 5/2003 |
| JP | A 2003-215036 | 7/2003 |
| JP | A-2003-344244 | 12/2003 |
| JP | A-2004-55183 | 2/2004 |
| JP | A 2004-117259 | 4/2004 |
| JP | A 2004-264146 | 9/2004 |
| JP | A 2004-317148 | 11/2004 |
| JP | A-2005-23249 | 1/2005 |
| JP | A-2005-24251 | 1/2005 |
| JP | A 2006-58009 | 3/2006 |
| JP | A-2006-184180 | 7/2006 |
| WO | WO 97/43609 | 11/1997 |
| WO | WO 99/46578 | 9/1999 |
| WO | WO 02/095376 A2 | 11/2002 |
| WO | WO 2005/077001 A2 | 8/2005 |
| WO | WO 2005/077001 A3 | 8/2005 |
| WO | WO 2005/111585 A2 | 11/2005 |
| WO | WO 2005/111585 A3 | 11/2005 |
| WO | WO 2006/118347 A1 | 11/2006 |
| WO | WO 2007/69786 A1 | 6/2007 |

OTHER PUBLICATIONS

Office Action issued in U.S. Appl. No. 11/918,650 on March 5, 2010.

Supplementary European Search Report issued in European Patent Application No. 06732512.6 mailed Mar. 17, 2010.

Office Action issued in U.S. Appl. No. 12/159,042 on Apr. 16, 2010.

Deguchi et al., "Development of direct and high response exhaust gas measurement (2); The techniques and the performance evaluation of the measurement equipment," *Preprints of Meeting on Automotive Engineers*, May 23, 2007, No. 12-07, pp. 25-28 (with Abstract).

Abe et al., "Advanced Combustion Control System by Real-time Measurement of CO, $O_2$ Concentration in Refuse Incineration Plant," *Mitsubishi Heavy Engineering Report*, vol. 38, No. 1, 2001, pp. 20-23 and 62 (with Abstract).

U.S. Appl. No. 12/309,584, filed Jan. 23, 2009 in the name of Masahiro Yamakage et al.

U.S. Appl. No. 12/159,042, filed Jun. 24, 2008 in the name of Masahiro Yamakage et al.

U.S. Appl. No. 12/083,521, filed Apr. 11, 2008 in the name of Katsutoshi Goto et al.

International Search Report issued in Application No. PCT/JP2007/066817 mailed Nov. 27, 2007.

International Search Report issued in Application No. PCT/JP2006/325566 mailed Jan. 23, 2007.

International Search Report issued in Application No. PCT/JP2006/309360 mailed May 30, 2006 (with Translation).

Supplementary European Search Report issued in European Patent Application No. 06843037 mailed on May 11, 2009.

Yamakage et al., "Development of Direct and Fast Response Gas Measurement," Publication No. 2008-01-0758, 2008.

Yamakage et al., "Development of Direct and High Response Gas Measurement," Publication No. 20070351, 2007 (with Abstract).

Davidy et al., "Development of Inverse Radiative Method for Measuring Gaseous and Particles Concentrations in the Exhaust Plumes by Using Remote Sensing Method," *41st AIAA/ASME/SAE/ASEE Joint Propulsion Conference & Exhibit*, AIAA 2005-3577, pp. 1-21, Jul. 2005.

Kubota et al., "Kogaku Gijutsu Handbook," pp. 1112-1117, Apr. 1997 (with Translation).

Yamakage et al., "Development of direct and high response exhaust gas measurement (1)," *Society of Automotive Engineers of Japan, Inc.*, Publication No. 20075153, No. 12-07, pp. 21-24, 2007 (with Translation).

U.S. Appl. No. 11/918,650, filed Oct. 17, 2007 in the name of Katsutoshi Goto et al.

* cited by examiner (a)

(b)

(c)

US 7,936,460 B2

SENSOR UNIT IN EXHAUST GAS ANALYZER

TECHNICAL FIELD

The present invention relates to an exhaust gas analyzer installed in an exhaust path for an engine or the like, which is capable of measuring the concentration of an exhaust-gas component contained in exhaust gas flowing through the exhaust path, and more particularly relates to a sensor unit in an exhaust gas analyzer.

BACKGROUND ART

Conventionally, a vehicle-mounted HC measurement device described in JP Published Patent Application No. 2004-117259 A (Patent Document 1) is available as an exhaust gas analyzer for car or the like. This vehicle-mounted HC measurement device is adapted to allow a NDIR (non-dispersive infrared spectroscopy) gas analyzer, an exhaust gas flowmeter and an arithmetic operation circuit to be installed in a vehicle, the NDIR for continuously measuring the HC (hydrocarbon) concentration in exhaust gas flowing through an exhaust tube connected with an engine, the exhaust gas flowmeter continuously measuring a flow rate of the exhaust gas flowing through the exhaust tube, and the arithmetic operation circuit performing arithmetic operation of an output from the NDIR gas analyzer and an output from the exhaust gas flowmeter to continuously calculate the THC (total hydrocarbon) amount in the exhaust gas.

Patent Document 1: JP Published Patent Application No. 2004-117259 A

DISCLOSURE OF THE INVENTION

Problem to be Solved by the Invention

Although the above-stated exhaust gas analyzer described in Patent Document 1 can facilitate measuring the THC in exhaust gas of a vehicle while the vehicle is moving on a real road, it is impossible to conduct the analysis of the exhaust gas in real time because the exhaust gas is transferred for the analysis of gas components from the exhaust path of the engine to the analysis section through a pipe. Further, in order to reduce the above-described units in size, analysis is carried out only to a limited component such as HC. At the development stage of an engine or attachments to the engine such as an exhaust gas purifier, it has been desired to provide an exhaust gas analyzer facilitating the measurement of components other than hydrocarbon in exhaust gas, such as nitrogen oxides and carbon monoxide, while being capable of measuring the concentration of the exhaust gas components in real time.

Then, the applicant of the present invention has developed an exhaust gas analyzer capable of facilitating the measurement of even a large number of exhaust gas components in exhaust gas such as nitrogen oxides and carbon monoxide in real time. The exhaust gas analyzer, as shown in FIG. 6, is composed of a plurality of sensor units 51A to 51D installed at a plurality of positions of an exhaust path of an exhaust tube 4 coupled to one of exhaust pipes 3 of an engine 2, a laser oscillation/light-receiving controller 6 emitting laser light to be applied to the exhaust gas, while receiving an electrical signal as an input from a light-receiving portion that receives the laser light, and an analyzer (personal computer) 7 that analyzes components contained in the exhaust gas and the concentrations thereof based on the light-emission intensity of the laser light to be applied to the exhaust gas and the light-reception intensity of the received laser light that has passed through the exhaust gas.

Since the sensor units 51A to 51D of the exhaust gas analyzer have the same configuration, the following describes one sensor unit 51 with reference to FIGS. 7 and 8.

The sensor unit 51 is disposed between a flange portion F of the exhaust tube 4 and a flange portion F of an exhaust tube 5 via gaskets 9, and these flange portions F and F are coupled using bolts (not illustrated), so that the sensor unit 51 is installed in an exhaust path of the exhaust gas.

The sensor unit 51 has a rectangular parallelepiped sensor base 55 made of metal. As shown in detail in FIG. 8, the sensor base 55 includes front and rear faces 55a and 55b orthogonal to the flowing direction of the exhaust gas, in which an exhaust gas passage opening 21 is formed at a center portion thereof, where the inner diameter of the exhaust gas passage opening 21 is the same as the inner diameter d of the circular cross section of the exhaust tube 4 so as not to disturb the flow of the exhaust gas. On an upper side face 55c perpendicular to the front and rear faces 55a and 55b, a sensor hole 22 is formed at a left part thereof to be orthogonal to the flowing direction of the exhaust gas, where the sensor hole 22 penetrates through the center of the wall thickness to the exhaust gas passage opening 21. On a lower side face 55d, a sensor hole 23 is formed at a right part thereof to be orthogonal to the flowing direction of the exhaust gas, where the sensor hole 23 penetrates through the center of the wall thickness from the edge to the exhaust gas passage opening 21.

To the sensor hole 22 of the sensor base 55, an irradiation portion 25 is attached, through which laser light is applied. The irradiation portion 25 is configured so as to be coupled to the laser oscillation/light-receiving controller 6 via an optical fiber 26, thus allowing laser light emitted from the laser oscillation/light-receiving controller 6 to be applied to the exhaust gas from the irradiation portion 25 via a collimate lens. To the sensor hole 23, a detector 27 is attached as a light-receiving portion that receives laser light applied from the irradiation portion 25 toward the exhaust gas passage opening 21 and that has passed through the exhaust gas. The detector 27 is coupled to the laser oscillation/light-receiving controller 6 via a signal line 28.

The sensor base 55 includes reflecting mirror insertion grooves 31 and 32 formed therein, which are parallel with each other so as to be opposed across the exhaust gas passage opening 21. At right and left of each of the reflecting mirror insertion grooves 31 and 32, screw holes 38 with female thread formed on the inner circumferential faces are bored so as to penetrate through to the exhaust gas passage opening 21. Reflecting mirrors 30 and 30 are inserted into the reflecting mirror insertion grooves 31 and 32 so that the respective reflecting planes face toward the exhaust gas passage opening 21, and the reflecting mirrors 30 are fixed thereto by screws 39 threadably mounted on the screw holes 38 from the exhaust gas passage opening 21.

Each reflecting mirror 30 includes a rectangular substrate made of quartz, sapphire, ceramic or the like with a thickness of several millimeters, on one side of which a thin film made of a reflective material with a high reflectivity such as gold, platinum, or titanium oxide matching with a laser wavelength is coated, on which a thin film of $MgF_2$ or $SiO_2$ is formed as a protective layer, thus configuring a reflecting surface.

Between the reflecting mirror insertion grooves 31, 32 and the exhaust gas passage opening 21, a plurality of laser light passage holes 56 with a small diameter are formed, so that the laser light applied from the irradiation portion 25 into the sensor hole 22 is reflected a plurality of times between the reflecting mirrors 30 and 30, and then arrives at the sensor hole 23.

The sensor base 55 further includes a right-side face 55e in which a heater insertion opening 33 is formed above and parallel to the reflecting mirror insertion groove 31, and includes a left-side face 55f in which a heater insertion opening 34 is formed below and parallel to the reflecting mirror insertion groove 32. Into these heater insertion openings 33 and 34, dew-condensation prevention heaters 35 are inserted, which are fixed thereto by screws 37 threadably mounted on screw holes 36. The dew-condensation prevention heaters 35 heat the reflecting mirrors 30 and 30 so as to prevent the condensation on the reflecting surfaces of the reflecting mirrors 30 and 30.

Then, in the exhaust gas analyzer shown in FIGS. 6 to 8, the laser light emitted from the laser oscillation/light-receiving controller 6 is applied to the exhaust gas from the irradiation portion 25 via the optical fiber 26, and the applied laser light is reflected a plurality of times between the reflecting mirrors 30 and 30 opposed to each other, and is received by the detector 27 after traveling a long distance through the exhaust gas, so as to be converted into an electrical signal. This electrical signal is input to the laser oscillation/light-receiving controller 6, and the laser oscillation/light-receiving controller 6 sends, to the analyzer 7, a differential signal between the intensity of the laser light emitted therefrom and the intensity of the received laser light.

The analyzer 7 calculates an absorption spectrum absorbed by the exhaust gas based on the differential signal transmitted from the laser oscillation/light-receiving controller 6 and analyzes this absorption spectrum, so that the exhaust gas components contained in the exhaust gas and the concentrations thereof can be measured in real time.

In the exhaust gas analyzer of FIGS. 6 to 8, the sensor units 51 are installed in the exhaust tubes 4 and 5, and exhaust gas is allowed to pass through the exhaust gas passage opening 21 from the exhaust tube 4, thus measuring the components and the concentrations of the exhaust gas in the same state as the exhaust gas flowing through the exhaust tube when the vehicle is actually moving. If the inner diameter of the exhaust tubes 4 and 5 is different from the inner diameter of the exhaust gas passage opening 21 of the sensor unit 51, then the flow of the exhaust gas will be disturbed, and the state of the flow will be different from the exhaust gas flowing through the exhaust tube when the vehicle is actually moving. Therefore, in order to measure the exhaust gas in the same state as the exhaust gas flowing through the exhaust tube when the vehicle is actually moving, the inner diameter of the exhaust gas passage opening 21 of the sensor unit 51 has to be the same as the inner diameter d of the exhaust tubes.

Meanwhile, currently there are a large number of types of cars including big-size cars, standard-sized cars, compact cars and the like available, and their exhaust tubes have different inner diameters depending on the car types. Furthermore, the inner diameters of the exhaust tubes will be different depending on the positions of the exhaust path, and therefore a large number of types of sensor units 51 having exhaust gas passage openings 21 with different inner diameters have to be prepared in order to enable the measurement of the exhaust gas at a plurality of positions of the exhaust path of these vehicles when the vehicles are moving. For example, for fifteen types of cars, each of which has three exhaust-tube connection positions on average, forty-five types of sensor units have to be prepared, which means expensive manufacturing cost.

Further, the exhaust gas flowing inside the exhaust tube will be at a high temperature as high as 1,000° C. in the exhaust tube 4 in the upstream closer to the engine 2, and will be at about 100° C. even at a low temperature section in the downstream. This means that the temperature of the sensor base 55 of the sensor units 51A to 51D will change in the range from about 20° C. as an ambient temperature to about 1,000° C. depending on the installation position. Thus, the sensor base 55 expands and shrinks repeatedly as the temperature changes, causing the displacement of the irradiation portion 25 and the reflecting mirrors 30 thereof, and the reflecting mirrors 30 may fail to reflect the laser light in correct directions, so that the laser light applied from the irradiation portion 25 may fail to arrive at the detector 27, resulting in a failure of the measurement.

Moreover, since the exhaust gas at a high temperature directly contacts with the exhaust gas passage opening 21 of the sensor base 55, the surface thereof may be damaged, and in that case the sensor base 55 as a whole has to be replaced even through other parts of the sensor base 55 still can be used.

In view of the above-stated problems, it is an object of the invention to provide a sensor unit in an exhaust gas analyzer at a low cost, the sensor unit being attachable to exhaust tubes so as to conform to their different inner diameters, and capable of stably measuring the concentration of exhaust gas components in exhaust gas when the vehicle is actually moving.

Means for Solving the Problem

In order to fulfill the above-stated object, a sensor unit in an exhaust gas analyzer of the present invention is installed in an exhaust path of exhaust gas and includes a sensor base including an exhaust gas passage opening through which exhaust gas passes, an irradiation portion from which laser light is applied and a light receiving portion, the irradiation portion and the light receiving portion being provided at the sensor base. Laser light applied from the irradiation portion to exhaust gas in the exhaust gas passage opening is received by the light receiving portion and a concentration of a component contained in the exhaust gas is measured based on the received laser light. The exhaust gas passage opening includes a through hole through which exhaust gas passes formed in an adjustment ring detachably fitted to an aperture formed in the sensor base, and the adjustment ring includes a circumferential face in which a laser-light passage portion is formed for allowing the laser light applied from the irradiation portion to arrive at the light receiving portion.

According to the sensor unit in an exhaust gas analyzer of the present invention, the laser light applied from the irradiation portion passes through the laser light passage portion in the circumferential face of the adjustment ring, passes through the exhaust gas, and is received by the light receiving portion, and the exhaust gas analyzer can measure the concentration of a component contained in the exhaust gas based on the received laser light. In the case where the through hole of the adjustment ring is damaged by the exhaust gas at a high temperature flowing through the through hole of the adjustment ring, the adjustment ring may be replaced with another one, whereby the sensor unit can be reused.

Further, the sensor base of the sensor unit according to the present invention includes reflecting mirrors disposed to be opposed to each other across the aperture, and the adjustment ring includes a circumferential face in which a laser-light passage portion is formed for letting the laser light reflected by the reflecting mirrors pass therethrough.

According to the sensor base of the sensor unit according to the present invention, the irradiated laser light passes through the laser light passage portion in the circumferential face of the adjustment ring, is reflected a plurality of times between the reflecting mirrors and travels a long distance through the exhaust gas, during which the laser light at a specific wavelength is absorbed by an exhaust gas component in the exhaust gas in accordance with the traveling distance, and therefore even an exhaust gas component of a low concentration can be measured for the concentration with accuracy.

The adjustment ring of the sensor unit according to the present invention is replaceable for fitting with an adjustment ring with a same outer shape and including a through hole with a different inner diameter. Further, in the sensor unit in an exhaust gas analyzer of the present invention, the adjustment ring is replaceable for fitting with a cylindrical adjustment ring with a same outer diameter and including a through hole with a different inner diameter.

In the adjustment ring of the sensor unit according to of the present invention, an adjustment ring with an inner diameter that is the same as the inner diameter of the exhaust tube is fitted to the aperture of the sensor base for replacement, whereby a sensor unit compatible with various inner diameters of exhaust tubes can be configured using one type of sensor base. The outer shape of the adjustment ring according to the present invention may be any shape as long as it has the same shape as the aperture of the sensor base. A circular shape can facilitate the manufacturing thereof, and an outer shape other than a circular shape can eliminate the necessity of the alignment of the laser light passage portion formed in the circumferential face of the adjustment ring when the adjustment ring is fitted to the aperture of the sensor base.

In the adjustment ring of the sensor unit according to the present invention, the laser-light passage portion formed in the circumferential face of the adjustment ring includes a plurality of small holes. In the adjustment ring of the sensor unit according to the present invention, when noise light occurs because the laser light applied into the exhaust gas passage opening is reflected by a dirt on the reflecting mirror, for example, such noise light is blocked off by a portion where the small holes are not formed, and the laser light for measurement only is allowed to pass through the small holes for laser-light passage, is reflected by the reflecting mirrors, and is received by the light receiving portion, whereby the concentration of an exhaust gas component in the exhaust gas can be measured with accuracy.

The adjustment ring of the sensor unit according to the present invention is made of a heat-insulating material. Further, the adjustment ring of the sensor unit according to the present invention is made of ceramic. According to the adjustment ring of the sensor unit of the present invention, heat at a high temperature from the exhaust gas flowing through the exhaust gas passage opening is blocked off by the adjustment ring made of ceramic with a heat insulation property, so that the heat at a high temperature from the exhaust gas is not conducted so much to the sensor base. Therefore, the distortion of the sensor base due to heat can be suppressed, so that the attachment positions of the reflecting mirrors, the irradiation portion and the light receiving portion are not displaced, and thus the concentrations of the exhaust gas components in the exhaust gas can be measured stably. Further, since the sensor base is not at a high temperature, there is no need to form the sensor base with a heat-resisting material, and therefore the material of the sensor base can be selected from a wider range of materials.

Effects of the Invention

In the sensor unit in an exhaust gas analyzer of the present invention, the adjustment ring with a through hole formed therein for letting exhaust gas pass therethrough is detachably fitted to the aperture formed in the sensor base, and in the circumferential face of the adjustment ring, the laser light passage portion is formed for allowing the laser light applied from the irradiation portion to arrive at the light receiving portion. Therefore, if the through hole of the adjustment ring is damaged due to a temperature of the exhaust gas or the like, the adjustment ring may be replaced with another one, whereby the sensor unit can be reused. Further, the adjustment ring is replaced for fitting with an adjustment ring with a through hole having a different inner diameter, whereby a sensor unit with exhaust gas passage openings of different inner diameters can be composed using one type of sensor base, which can be installed in exhaust tubes with various inner diameters.

Figure 1:
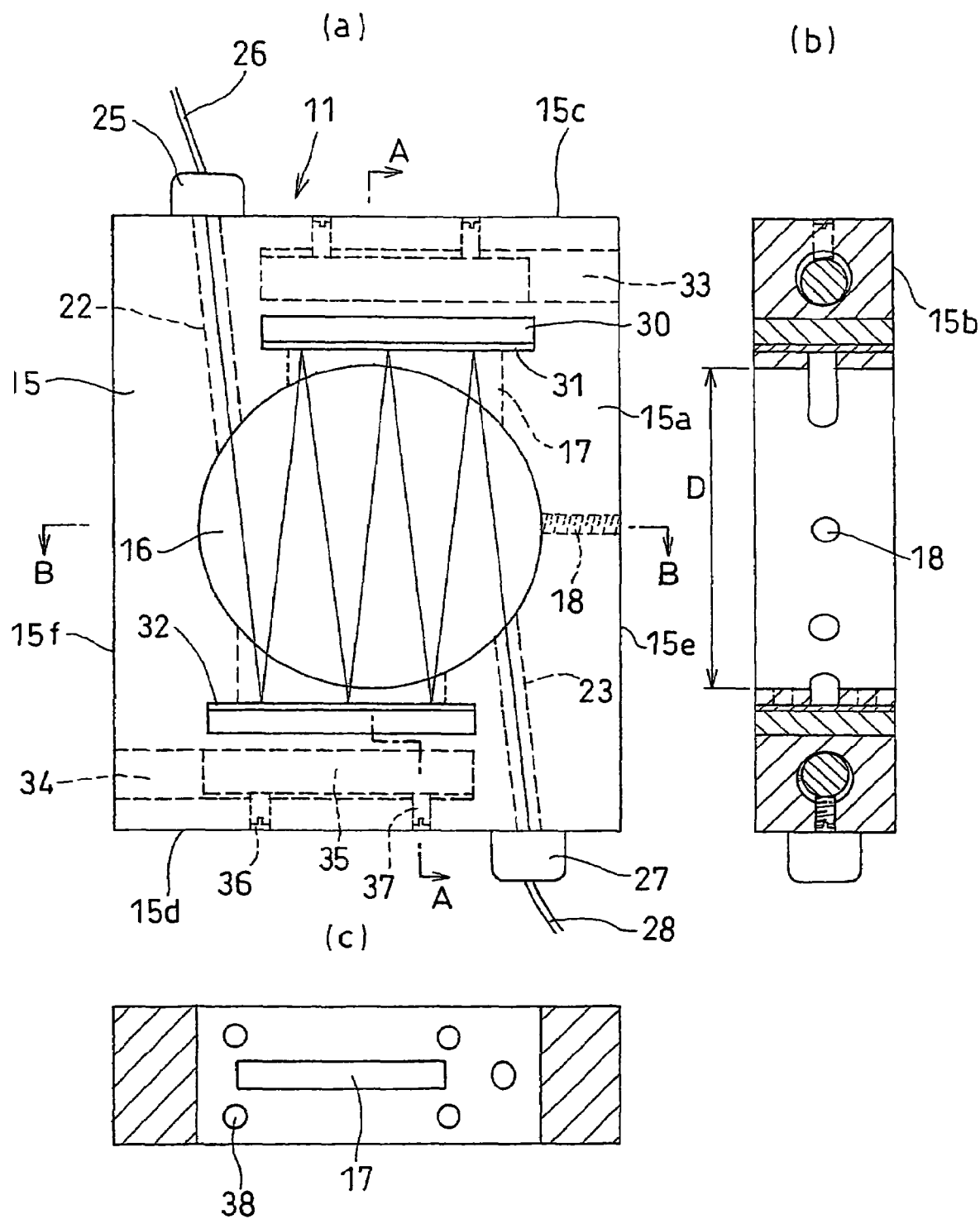
FIG. 1 illustrates a sensor base in a sensor unit according to one embodiment of the present invention, where (a) is a front view of the sensor base, (b) is a cross-sectional view taken along the line A-A of (a), and (c) is a cross-sectional view taken along the line B-B of (a).

In these drawings, the respective reference numbers denote the followings:
2 engine
3 each exhaust pipe
4 exhaust tube
5 exhaust tube
6 laser oscillation/light-receiving controller
7 computer
11 sensor unit
15 sensor base
16 aperture
17 laser light passage slit
18 bolt insertion hole
19 bolt
21 exhaust gas passage opening
22 sensor hole
23 sensor hole
25 irradiation portion
26 optical fiber
27 detector
28 signal line
30 reflecting mirror 31, 32 reflecting mirror insertion groove
33, 34 heater insertion opening
35 dew-condensation prevention heater
36 screw hole
37 screw
38 screw hole
39 screw
40, 40a, 40b, 40c adjustment ring
41 laser-light passage small hole.

BEST MODE FOR CARRYING OUT THE INVENTION

Figure 6:
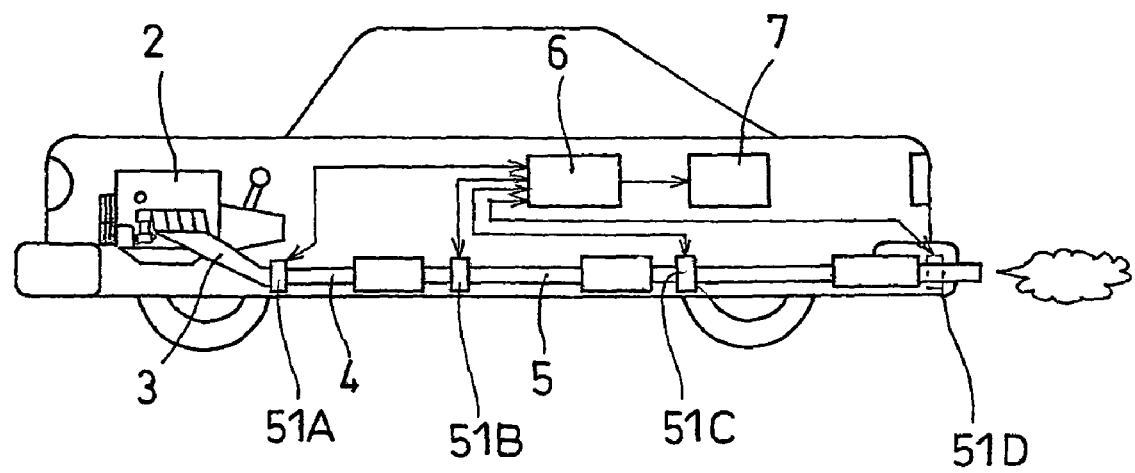
FIG. 6 shows the configuration of major parts showing a state where an exhaust gas analyzer invented by the applicant of the present invention is mounted in a vehicle.
Figure 7:
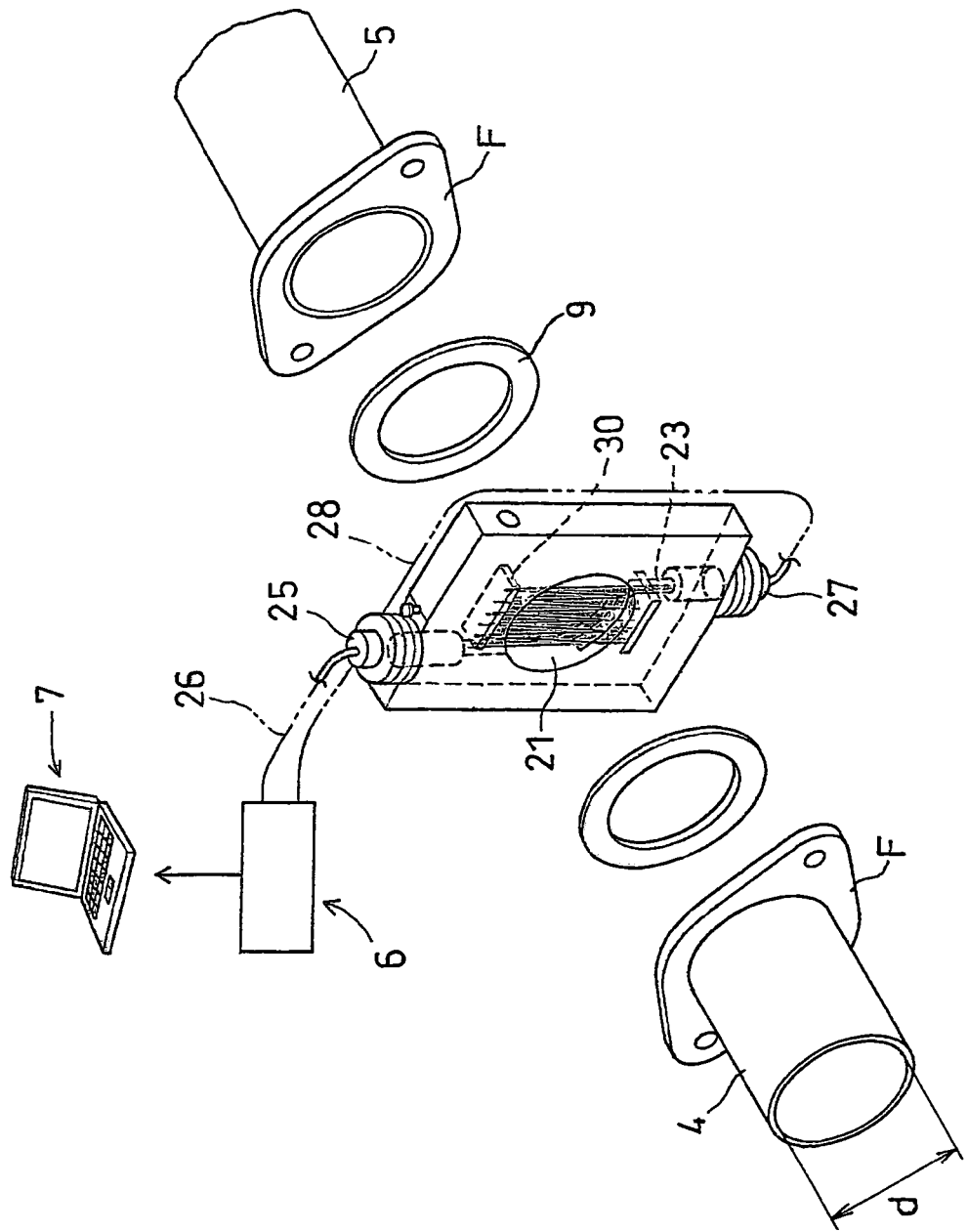
FIG. 7 is a perspective view of a state where the sensor unit of the exhaust gas analyzer is removed from an exhaust tube.

FIG. 1 illustrates a sensor base in a sensor unit according to Embodiment 1 for implementing the present invention, where (a) is a front view of the sensor base, (b) is a cross-sectional view taken along the line A-A of (a), and (c) is a cross-sectional view taken along the line B-B of (a). The same reference numerals have been assigned to the elements with the same configurations as those in the sensor unit of FIGS. 6 to 8.

As shown in FIG. 1, a sensor base 15 of a sensor unit 11 of the present invention is made of metal and has a rectangular parallelepiped shape. The sensor base 15 includes front and rear faces 15a and 15b orthogonal to the flowing direction of the exhaust gas, in which a large-diameter aperture 16 with a diameter D is formed at a center portion thereof. On an upper side face 15c perpendicular to the front and rear faces 15a and 15b, a sensor hole 22 is formed at a left part thereof to be orthogonal to the flowing direction of the exhaust gas, where the sensor hole 22 penetrates through the center of the wall thickness to the aperture 16. On a lower side face 15d, a sensor hole 23 is formed on a right part thereof to be orthogonal to the flowing direction of the exhaust gas, where the sensor hole 23 penetrates through the center of the wall thickness to the aperture 16. The diameter D of the aperture 16 has to be made larger than the inner diameter d of an exhaust tube of a vehicle as a target of the measurement of exhaust gas by the sensor unit 11.

To the sensor hole 22 of the sensor base 15, an irradiation portion 25 is attached, through which laser light is applied. The irradiation portion 25 is configured so as to be coupled to a laser oscillation/light-receiving controller 6 via an optical fiber 26, thus allowing laser light emitted from the laser oscillation/light-receiving controller 6 to be applied to the exhaust gas from the irradiation portion 25 via a collimate lens. To the sensor hole 23, a detector 27 is attached as a light-receiving portion that receives laser light applied from the irradiation portion 25 toward the exhaust gas passage opening 21 and that has passed through the exhaust gas, where the detector 27 is coupled to the laser oscillation/light-receiving controller 6 via a signal line 28.

The front and rear faces 15a and 15b of the sensor base 15 include reflecting mirror insertion grooves 31 and 32 formed therein, which are parallel with each other so as to be opposed across the aperture 16. At right and left of each of the reflecting mirror insertion grooves 31 and 32, screw holes 38 are bored so as to penetrate through to the aperture 16. Reflecting mirrors 30 and 30 are inserted into the reflecting mirror insertion grooves 31 and 32 so that the respective reflecting planes face toward the aperture 16, and the reflecting mirrors 30 are fixed thereto by screws threadably mounted on the screw holes 38 from the aperture 16.

Each reflecting mirror 30 includes a rectangular substrate made of quartz, sapphire, ceramic or the like with a thickness of several millimeters, on one side of which a thin film made of a reflective material with a high reflectivity such as gold, platinum, or titanium oxide matching with a laser wavelength is coated, on which a thin film of $MgF_2$ or $SiO_2$ is formed as a protective layer so as to configure a reflecting surface.

Between the reflecting mirror insertion grooves 31, 32 and the aperture 16, a long and narrow laser light passage slit 17 is formed, so that the laser light can be reflected a plurality of times between the reflecting mirrors 30 and 30.

The sensor base 15 further includes a right-side face 15e in which a heater insertion opening 33 is formed above and parallel to the reflecting mirror insertion groove 31, and includes a left-side face 15f in which a heater insertion opening 34 is formed below and parallel to the reflecting mirror insertion groove 32. Into these heater insertion openings 33 and 34, dew-condensation prevention heaters 35 are inserted, which are fixed thereto by screws 37 threadably mounted on screw holes 36. The dew-condensation prevention heaters 35 heat the reflecting mirrors 30 and 30 so as to prevent the condensation on the reflecting surfaces of the reflecting mirrors 30 and 30.

At the right-side face 15e of the sensor base 15, a bolt insertion hole 18 with a female thread formed on the inner surface is formed so as to penetrate through to the aperture 16.

Figure 2:
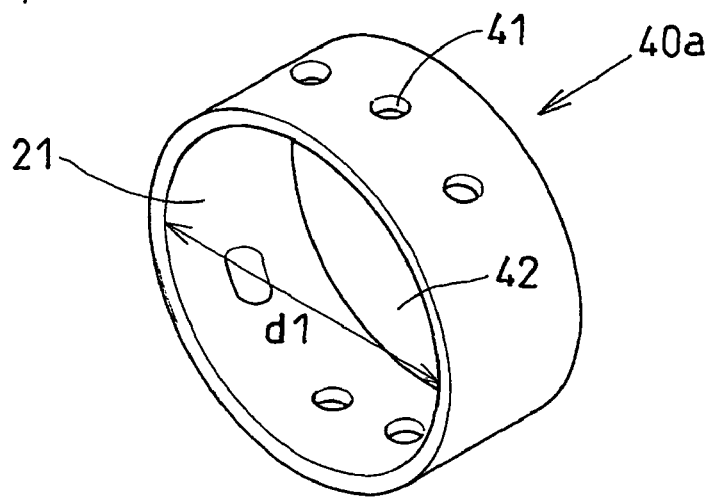
FIG. 2 is a perspective view of an adjustment ring in a sensor unit according to one embodiment of the present invention.
Figure 2:
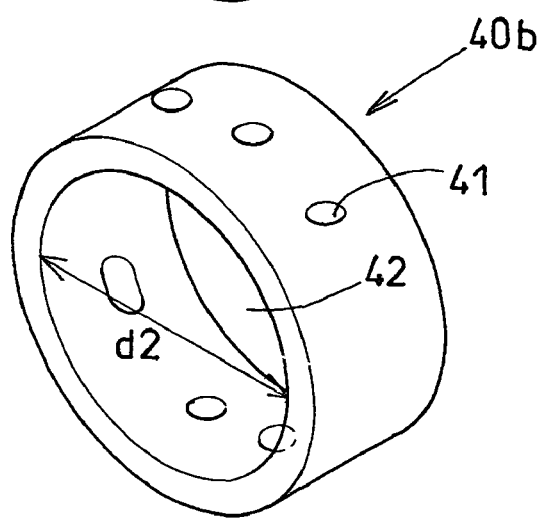
Figure 2:
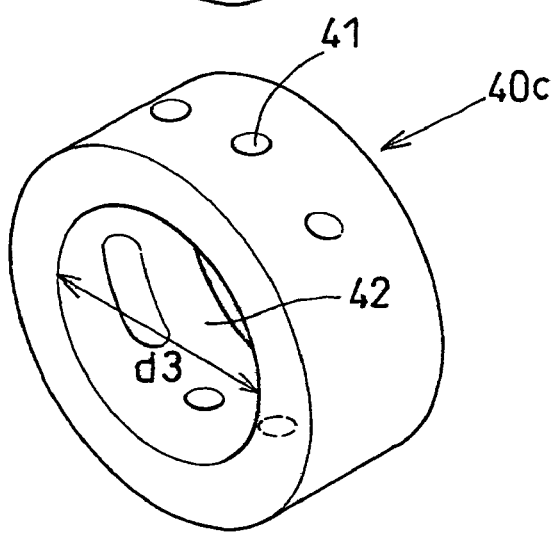

FIGS. 2 (a) to (c) are perspective views showing adjustment rings 40 to be fitted to the aperture 16 of the sensor base 15. The adjustment rings 40a, 40b and 40c are made of ceramic and are formed in a cylindrical shape, where the outer diameter of these rings is approximately the same as the inner diameter D of the aperture 16 of the sensor base 15, and through holes 42 formed at the center thereof function as an exhaust gas passage opening 21 through which exhaust gas pass when the sensor unit 11 is installed in the exhaust path.

The width of the adjustment rings 40a, 40b, and 40c is formed to be the same as the thickness of the sensor base 15, and a plurality of laser-light passage small holes 41, 41 . . . are formed in circumferential faces of the adjustment rings 40a, 40b and 40c to configure a laser-light passage portion. The laser light applied from the irradiation portion 25 passes through the laser-light passage small holes 41, 41 . . . so as to be reflected a plurality of times between the reflecting mirrors 30 and 30, and then to be received by the detector 27 as a light-receiving portion. These laser-light passage small holes 41, 41 . . . allow only the laser light reflected precisely by the reflecting mirrors 30 to pass therethrough, but block off the laser light deviating from the optical path, so that the measurement accuracy can be enhanced.

In FIG. 2, the adjustment ring 40a of (a) is for big-size cars with an exhaust tube of a large inner diameter, where the thickness of the ring is formed small so as to allow the through hole 42 serving as the exhaust gas passage opening 21 to have a large inner diameter d1, the adjustment ring 40c of (c) is for compact size cars with an exhaust tube of a small inner diameter, where the thickness of the ring is formed large so as to allow the through hole 42 serving as the exhaust gas passage opening 21 to have a small inner diameter d3, and the adjustment ring 40b of (b) is for medium-size cars, where the inner diameter d2 of the through hole 42 is formed to be a medium size between the adjustment ring 40a and the adjustment ring 40c.

Although FIG. 2 illustrates three types of adjustment rings 40a, 40b and 40c, there is a need to prepare adjustment rings 40 with through holes 42 of different inner diameters in number corresponding to the number of types of inner diameters of the exhaust tubes as a target of the exhaust gas measurement.

Figure 3:
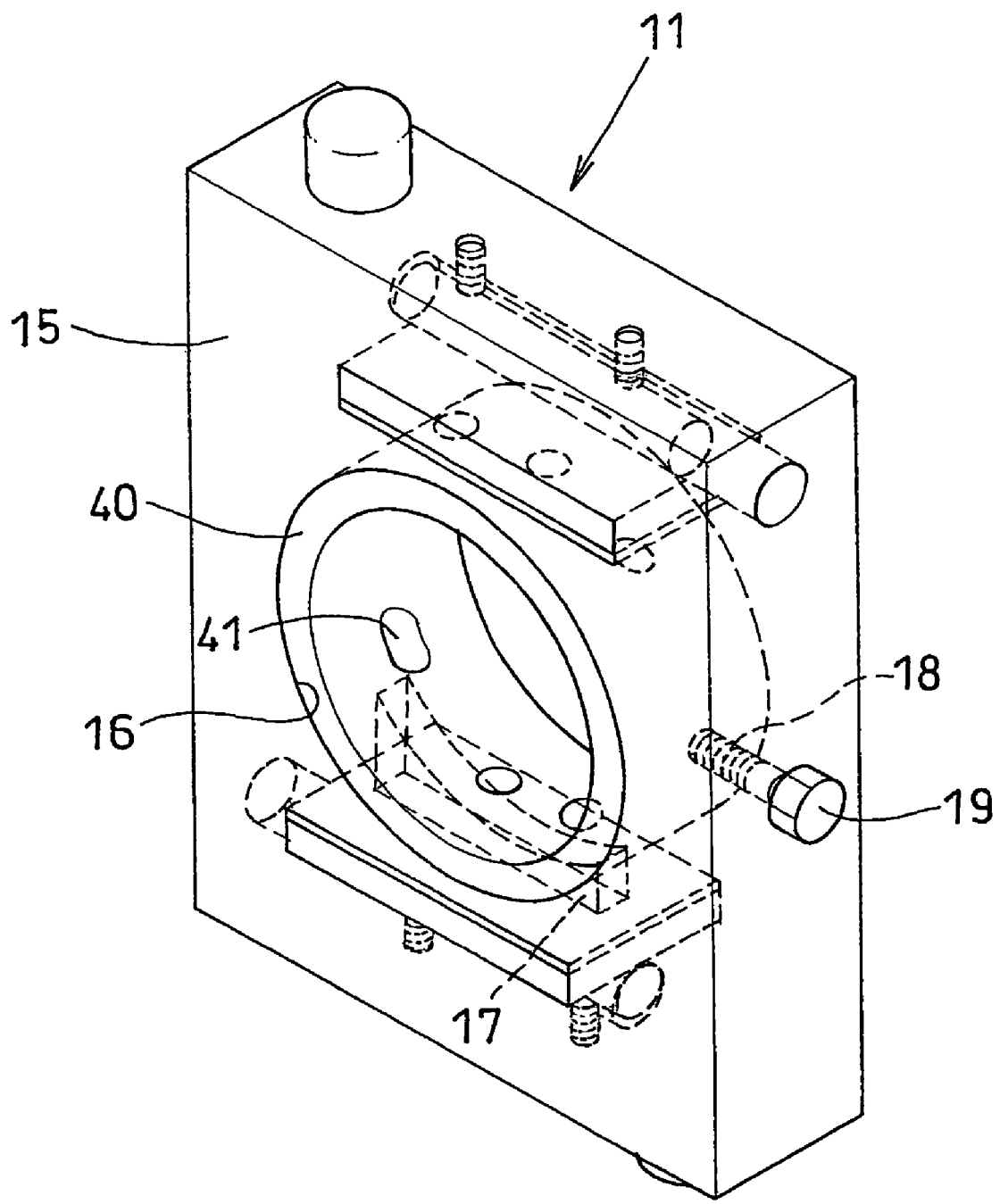
FIG. 3 is a perspective view of a sensor unit according to one embodiment of the present invention.

Then, as shown in FIG. 3, an adjustment ring 40 with an inner diameter that is the same as the inner diameter of the exhaust tube 4 of the vehicle as a target of the exhaust gas measurement is fitted to the aperture 16 of the sensor base 15, and a bolt 19 is threadably mounted on the bolt insertion hole 18 so as to fix and fit the adjustment ring 40 to the sensor base 15, thus configuring the sensor unit 11.

Such a sensor unit 11 is disposed between a flange F of an exhaust tube 4 and a flange F of an exhaust tube 5 via gaskets, and the flanges F and F are coupled by bolts and nuts, whereby the sensor unit 11 is installed in the exhaust tubes 4 and 5.

Then, when the exhaust gas flowing through the exhaust gas passage opening 21 is irradiated with the laser light from the irradiation portion 25, the irradiated laser light passes through the sensor hole 22, the laser-light passage small holes 41 of the adjustment ring 40 and the laser light passage slit 17 and is reflected by a reflecting mirror 30. After being reflected between the reflecting mirrors 30 and 30 a plurality of times, the laser light passes through the sensor hole 23 and is received by the detector 27 to be converted into an electrical signal. This electrical signal is input to the laser oscillation/light-receiving controller 6 via the signal line 28, and the laser oscillation/light-receiving controller 6 sends a differential signal between the intensity of the laser light emitted therefrom and the intensity of the received laser light to an analyzer (computer) 7. The analyzer 7 calculates an absorption spectrum absorbed by the exhaust gas based on the differential signal between the intensity of the laser light emitted and the intensity of the laser light received and analyzes this absorption spectrum, whereby the exhaust gas components contained in the exhaust gas and the concentrations thereof can be measured in real time.

The irradiated laser light is reflected a plurality of times between the reflecting mirrors 30 and 30 opposed to each other and travels a long distance through the exhaust gas, during which the laser light at a specific wavelength is absorbed by an exhaust gas component in the exhaust gas in accordance with the traveling distance, and therefore even an exhaust gas component of a low concentration can be measured with accuracy.

Figure 4:
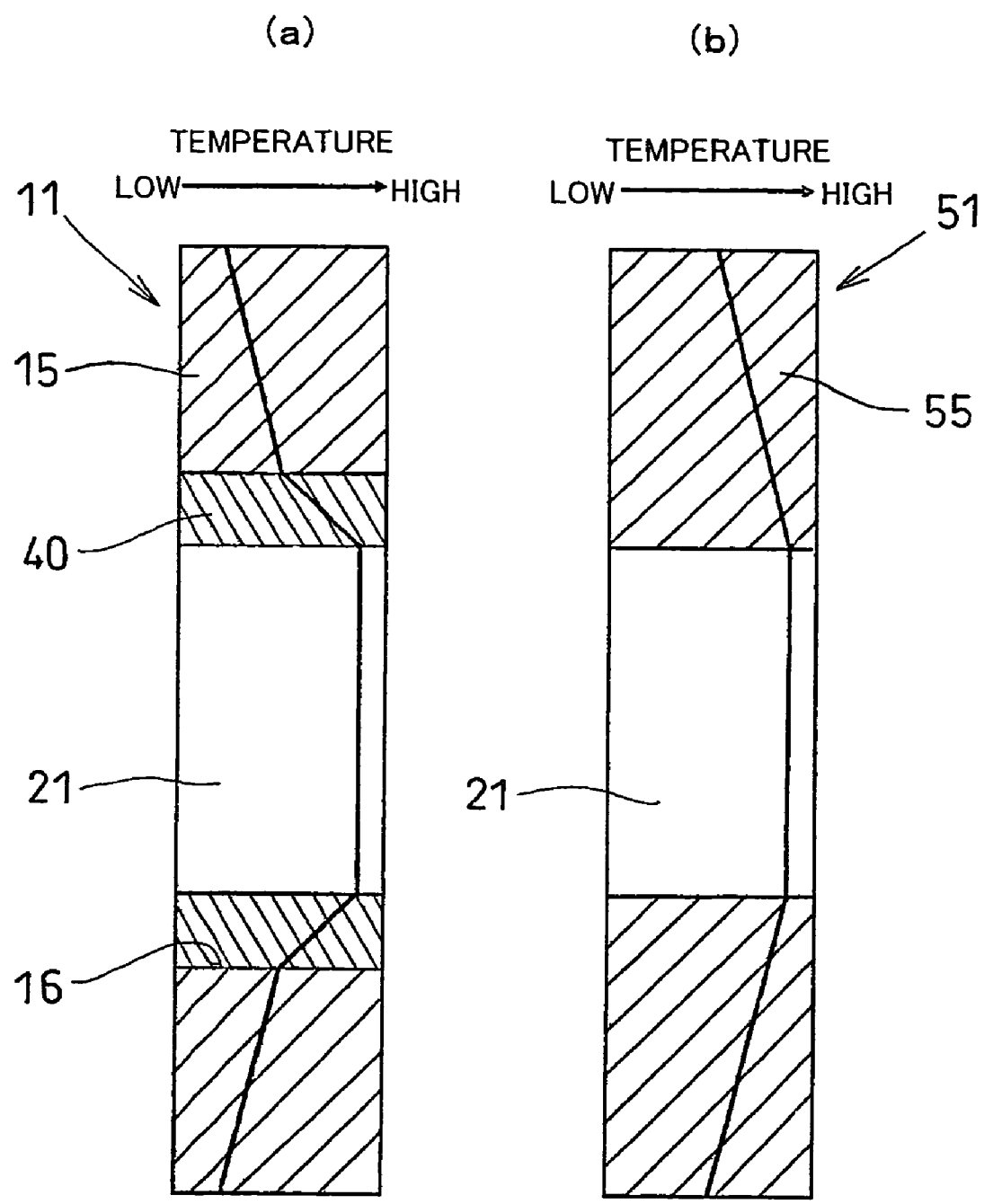
FIG. 4 is for explaining heat conduction states of exhaust gas in a sensor unit according to one embodiment of the present invention and in a sensor unit without the adjustment ring fitted thereto, where (a) shows one with an adjustment ring, and (b) shows one without an adjustment ring.

FIG. 4 is for explaining heat conduction states of the exhaust gas in the sensor base 15 to which the adjustment ring 40 is fitted and the sensor base 55 to which the adjustment ring is not fitted, where the sensor unit 11 and the sensor unit 51 include exhaust gas passage openings 21 of the same inner diameter formed therein.

In the sensor base 15 with the adjustment ring 40 fitted thereto, the adjustment ring 40 is made of ceramic with good insulation effectiveness, which means less heat conduction in the adjustment ring 40, and therefore it can prevent an increase in temperature of the aperture 16 of the sensor base 15 due to the temperature of the exhaust gas. Therefore, as compared with one without the adjustment ring fitted thereto, an increase in temperature of the sensor base 15 is smaller, thus making it possible to reduce a temperature difference between the interior and the exterior of the sensor base 15. Since the distortion of the sensor base 15 due to heat of the exhaust gas flowing through the exhaust gas passage opening 21 can be suppressed, so that the displacement of the attachment positions of the reflecting mirrors 30 and the laser irradiation portion 25 can be made small, and thus the concentrations of the exhaust gas components in the exhaust gas can be measured stably. Further, since the sensor base 15 is not at a very high temperature even at the aperture 16, there is no need to form the sensor base with a heat-resisting material, and therefore the material of the sensor base can be selected from a wider range of materials.

Figure 5:
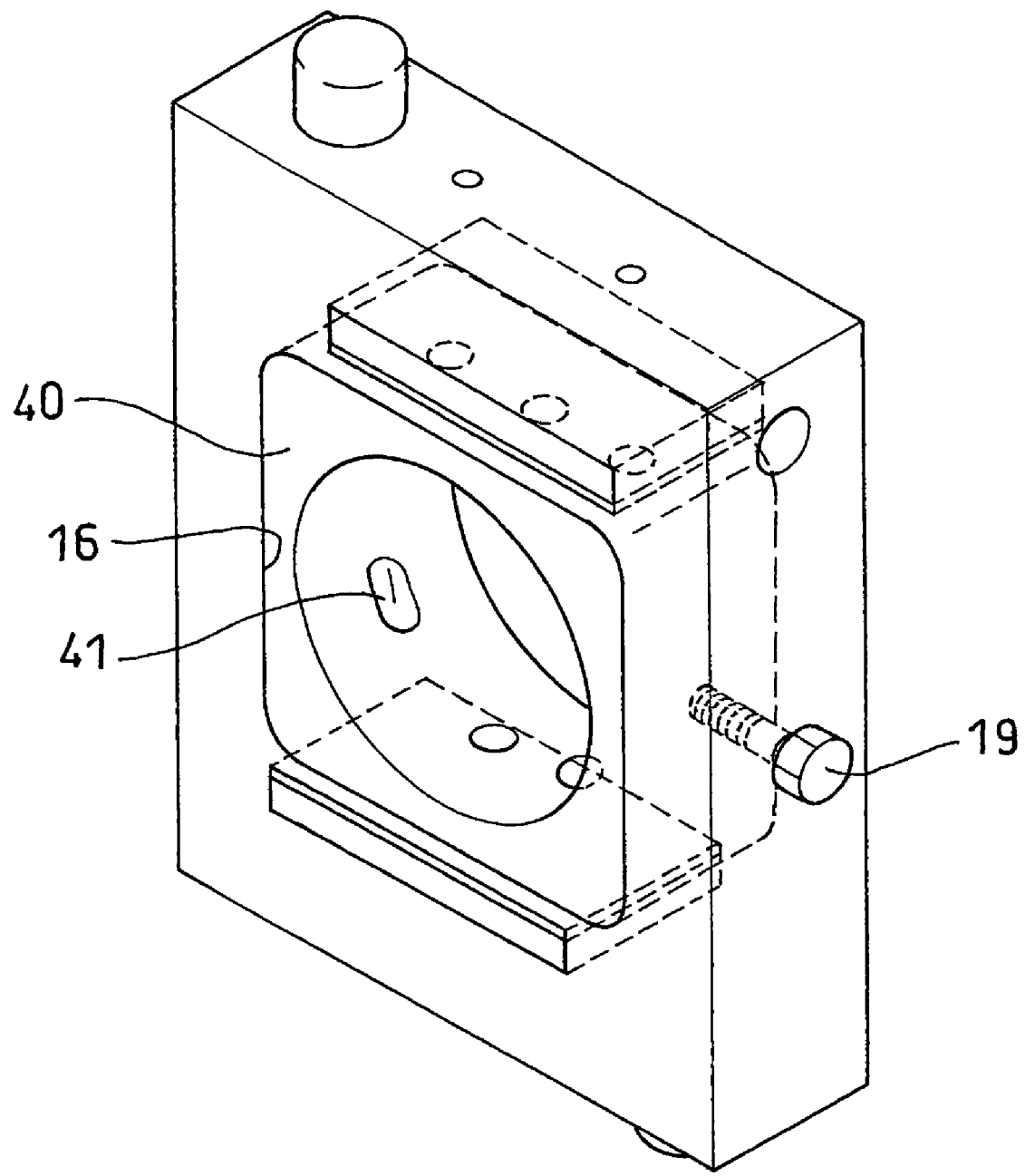
FIG. 5 is a perspective view of a sensor unit to which an adjustment ring according to another embodiment of the present invention is fitted.

FIG. 5 is a perspective view of a sensor unit to which an adjustment ring according to another embodiment of the present invention is fitted, where an aperture 16 of a sensor base 15 is formed to be rectangular. The outer shape of the adjustment ring 40 also is formed to be rectangular so as to be fitted to the aperture 16 of the sensor base, and the inner circumferential face is formed to be circular corresponding to the shape of the exhaust tube. The outer shape of the adjustment ring 40 other than a circular shape can eliminate the alignment of the sensor base 15 with the adjustment ring 40 that is for allowing the laser light applied from the irradiation portion to be reflected between the reflecting mirrors 30 and 30 and then to be received the detector 27.

Figure 8:
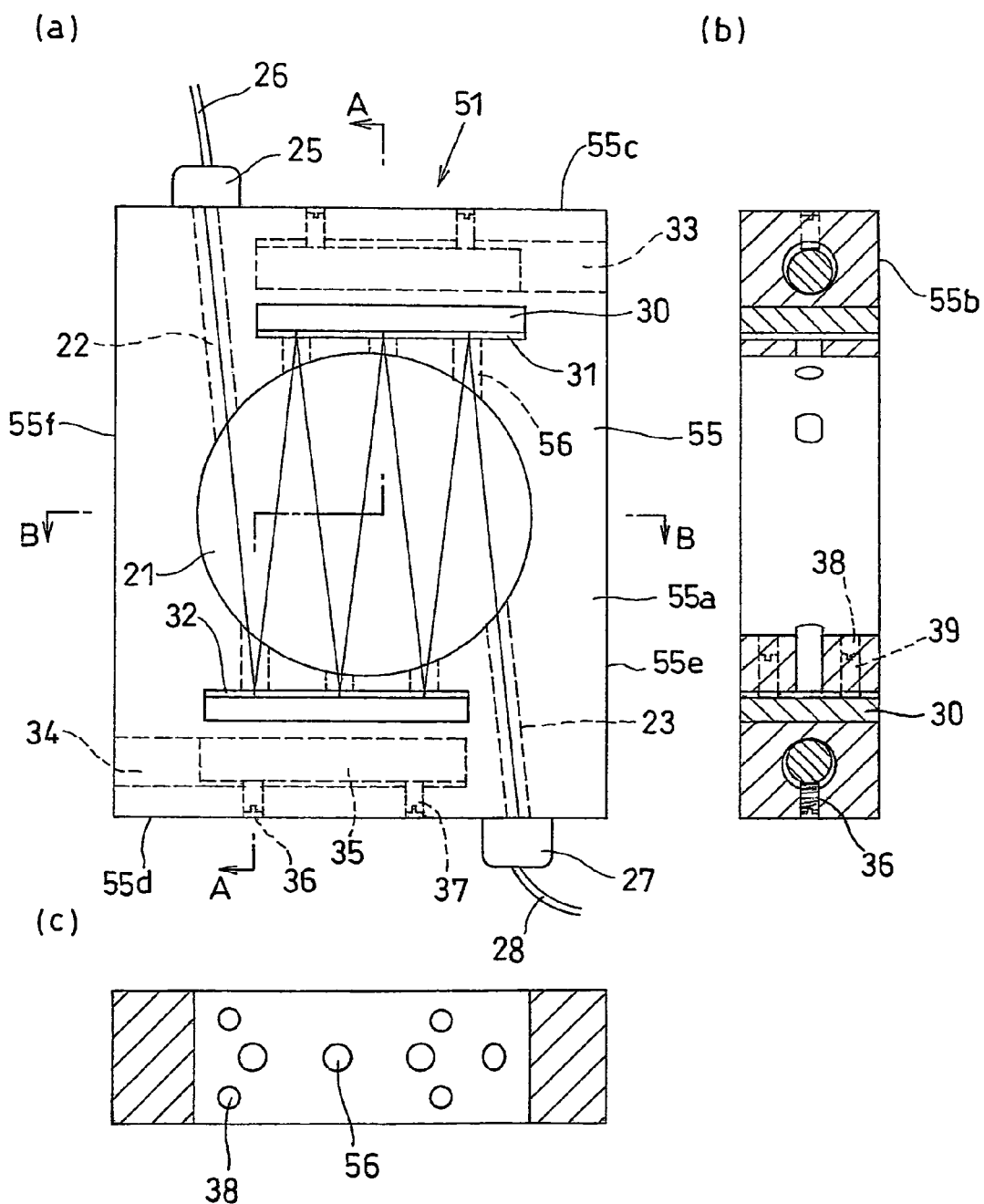
FIG. 8 shows the sensor unit of the exhaust gas analyzer, where (a) is a front view of the sensor unit, (b) is a cross-sectional view taken along the line A-A of (a), and (c) is a cross-sectional view taken along the line B-B of (a).

Although that is a detailed description of the embodiments of the present invention, the present invention is not limited to the above-stated embodiments, and the design may be modified variously without departing from the spirits of the present invention defined in the attached claims. For instance, in the above embodiment, the laser light passage slit 17 for the laser light in the sensor base 15 is formed as an elongate hole. However, as shown in FIG. 8, this may be a plurality of small holes. In this case, the laser-light passage small holes 41 of the adjustment ring 40 can be made a slit. Furthermore, in the sensor unit of the above-described embodiments, the reflecting mirrors 30 and 30 are disposed to be opposed to each other across the aperture 16 of the sensor base 15. However, the sensor unit may include a sensor base without the reflecting mirrors 30 and 30 disposed therein, where the laser light applied from the irradiation portion traverses the exhaust gas passage opening while passing through the exhaust gas, and then is received by the light-receiving portion.

The invention claimed is:

1. A sensor unit in an exhaust gas analyzer, the sensor unit being installed in an exhaust path of exhaust gas and comprising a sensor base including an exhaust gas passage opening through which exhaust gas passes, an irradiation portion from which laser light is applied and a light receiving portion, the irradiation portion and the light receiving portion being provided at the sensor base, wherein laser light applied from the irradiation portion to exhaust gas in the exhaust gas passage opening is received by the light receiving portion and a concentration of a component contained in the exhaust gas is measured based on the received laser light, wherein the exhaust gas passage opening comprises a through hole through which exhaust gas passes formed in an adjustment ring detachably fitted to an aperture formed in the sensor base, and wherein the adjustment ring includes a circumferential face in which a laser-light passage portion is formed for allowing laser light applied from the irradiation portion to arrive at the light receiving portion.

2. The sensor unit in an exhaust gas analyzer according to claim 1, wherein the sensor base includes reflecting mirrors disposed to be opposed to each other across the aperture, and the adjustment ring includes a circumferential face in which a laser-light passage portion is formed for letting laser light reflected by the reflecting mirrors pass therethrough.

3. The sensor unit in an exhaust gas analyzer according to claim 1, wherein the adjustment ring is replaceable with an adjustment ring with a same outer shape and including the through hole with a different inner diameter.

4. The sensor unit in an exhaust gas analyzer according to claim 1, wherein the adjustment ring is replaceable with a cylindrical adjustment ring with a same outer diameter and including a through hole with a different inner diameter.

5. The sensor unit in an exhaust gas analyzer according to claim 1, wherein the laser-light passage portion formed in the circumferential face of the adjustment ring includes a plurality of small holes.

6. The sensor unit in an exhaust gas analyzer according to claim 1, wherein the adjustment ring is made of a heat-insulating material.

7. The sensor unit in an exhaust gas analyzer according to claim 1, wherein the adjustment ring is made of ceramic.

* * * * *